United States Patent
Tello

(10) Patent No.: US 9,295,753 B1
(45) Date of Patent: Mar. 29, 2016

(54) AMNIOTIC MEMBRANE PREPARATION AND DEVICE FOR USE AS A LENS OR AS A DRESSING FOR PROMOTING HEALING

(71) Applicant: Celso Tello, Queens, NY (US)

(72) Inventor: Celso Tello, Queens, NY (US)

(*) Notice: Subject to any disclaimer, the term of this patent is extended or adjusted under 35 U.S.C. 154(b) by 122 days.

(21) Appl. No.: 13/933,747

(22) Filed: Jul. 2, 2013

Related U.S. Application Data

(60) Provisional application No. 61/667,011, filed on Jul. 2, 2012.

(51) Int. Cl.
*B29C 63/02* (2006.01)
*A61K 35/48* (2015.01)
*A61L 26/00* (2006.01)

(52) U.S. Cl.
CPC ........... *A61L 26/0057* (2013.01); *A61L 26/009* (2013.01); *A61L 26/0033* (2013.01); *A61L 26/0066* (2013.01)

(58) Field of Classification Search
CPC ............................ A61K 9/0051; A61K 9/0048
USPC ................. 424/428, 93.7, 582; 623/5.16
See application file for complete search history.

(56) References Cited

U.S. PATENT DOCUMENTS

| | | |
|---|---|---|
| 7,494,802 B2 | 2/2009 | Tseng et al. |
| 7,871,646 B2 | 1/2011 | Ghinelli |
| 8,071,135 B2 | 12/2011 | Liu et al. |
| 8,105,634 B2 | 1/2012 | Liu et al. |
| 8,158,141 B2 | 4/2012 | Chen |
| 8,182,840 B2 | 5/2012 | Tseng et al. |
| 2007/0031471 A1 | 2/2007 | Peyman |
| 2008/0286378 A1 | 11/2008 | Behrens et al. |

OTHER PUBLICATIONS

Fujisato T et al.; Title: Cross-linking of amniotic membranes; J Biomater Sci Polym Ed. 1999;10(11):1171-81.*
Spoerl E. et al; title: Cross-Linking of Human Amniotic Membrane by Glutaraldehyde; vol. 36, No. 2, 2004; Abstract.*

* cited by examiner

*Primary Examiner* — Johann R Richter
*Assistant Examiner* — Yanzhi Zhang
(74) *Attorney, Agent, or Firm* — Levisohn Berger LLP

(57) ABSTRACT

A method for the producing a complex containing human or mammal's amniotic membrane/placental extract with or without collagen. Compositions containing the complexes and therapeutic methods using the complexes are provided. In addition, the invention relates to a method of controlling the absorption rates of amniotic membrane/extract and/or placental extract by combining any one of them with collagen having a desired degradation rate.

4 Claims, No Drawings

AMNIOTIC MEMBRANE PREPARATION AND DEVICE FOR USE AS A LENS OR AS A DRESSING FOR PROMOTING HEALING

RELATED APPLICATIONS

This Application claims the benefit of U.S. Provisional Appl. Ser. No. 61/667,011 filed on Jul. 2, 2012—the contents of which are incorporated by reference herein.

BACKGROUND OF THE INVENTION

Treatment of ocular surface disorders requires medical and surgical intervention, both acutely and in the long term. Regardless of the underlying causes involved, the common goals of management include controlling inflammation and promoting ocular surface healing with maximal visual rehabilitation. Various medical therapies have been used to achieve these objectives.

Amniotic membrane (AM) graft has been used in ophthalmology for several indications because of its beneficial effects. Previous studies revealed that early intervention with amniotic membrane transplantation (AMT) results in marked reduction of inflammation, rapid restoration of the ocular surface, and improved visual acuities while preventing cicatricial complications (Dua 2004). However, surgically performed AMT renders a relatively high cost and potentially unnecessary surgical trauma in such compromised eyes. Furthermore, the membrane patch usually dissolves within several days so that multiple sessions of AMT may be required. Recently, a self-retaining AM mounted on a double ring system (Prokera, Biotissue Inc., Miami Fl.) has been effectively used to promote healing and reduce corneal scarring in acute chemical burn and bacterial keratitis (Sheha 2009), however, patients experienced ocular discomfort from the ring and incomplete healing due to improper centration of the device.

Recent studies have shown that topical amniotic membrane extract (AME) has comparable effect to AMT in promoting epithelialization, decreasing inflammation, and suppressing corneal neovascularization. However amniotic membrane extract lacks the physical characteristics of a bandage and as such it cannot be used as a patch graft (Sheha 2010).

In summary, amniotic membrane dissolves too rapidly for prolonged use and it requires application by surgical intervention. Amniotic membrane retained by a ring does not require surgery—but it is obtrusive, not well tolerated and as a result it suffers from sub-optimal therapeutic outcomes. Amniotic membrane extract—though it shares the healing qualities of intact amniotic membrane—it does not have the physical characteristics of a patch.

There is, therefore, a need for a delivery device that is a self-retaining patch that is applied using non-surgical means, is well tolerated by patients, lasts for an extended period of time and does not require a mechanical ring structure for maintaining the patch in position.

SUMMARY OF THE INVENTION

The invention described herein is a medical, multi-purpose ophthalmic lens, which is made of amniotic/placental extract with or without different collagen proteins. The amniotic membrane extract is preferably cross-linked to a collagen material to form an amniotic membrane/collagen patch. The amniotic patch is formed in the general shape of a contact lens that can easily be placed on the surface of the eye to deliver the AM properties to treat and protect the ocular surface. The inventive patch achieves the therapeutic benefits of amniotic membrane without the need for surgery or a retaining ring. Moreover, because the amniotic membrane extract is cross-linked to other stable molecules—it lasts longer than pure amniotic membrane. The patch is manufactured as a dissolvable material to allow the naturally occurring enzymes in the tear film to dissolve the patch over a period of time without the need for removal after healing. (Note that the novel amniotic/placental extract with or without different collagen proteins described herein is sometimes referred to as the AmnioShield).

The inventive amniotic membrane device is applied to an eye in the same manner as one would apply a conventional contact lens used for vision correction—obviating the need for surgical intervention or for a retaining ring. Because the amniotic membrane extract is embedded in a carrier (such as collagen)—the bandage effect and the therapeutic benefits of amniotic membrane extract are realized—yet with the comfort of a contact lens.

DETAILED DESCRIPTION OF THE INVENTION

In a preferred embodiment of the invention, amniotic membrane extract is supported by a collagen-based carrier or filler. The collagen-based carrier is formable into various shapes and configurations according to different embodiments of the invention.

Collagen is the primary structural protein in the mammalian body. Through specific self-aggregation and crosslinking, collagen can form fibers of unusual strength and stability. These unique characteristics define its basic qualities as a biomaterial suitable for medical products. In addition, it is a natural material of low immunogenicity and is therefore seen by the body's immune system as a normal constituent rather than foreign matter.

Although collagen is universal in the mammalian body, those tissues rich in fibrous collagen such as skin and tendon are commonly used to generate collagen. Animal derived collagen is the main source; however numerous different sources including the human placenta have been described. Collagen type I is by far the most abundant and the majority of collagen materials for biomedical applications are based on this type. It will be understood that any of various collagen sources—including those listed above may be used in different embodiments of the invention.

Collagen can be processed into a number of forms such as sheets, tubes, sponges, powders, fleeces, injectable solutions and dispersions, all of which have found use in medical practice. Specific degradation rates can be adjusted in the context of various applications.

In a preferred embodiment, a collagen carrier is formed into the general shape of a contact lens and amniotic membrane extract is either embedded in the collagen carrier or chemically linked thereto.

In addition to its shape-maintaining capabilities, different types of collagens have different degradation rates. This property allows clinicians to manipulate the absorption time of amniotic membrane extract in different embodiments of the invention. For instance, if slow absorption is desired—then a collagen with a slow degradation rate may be utilized, whereas, if more rapid absorption is desired a collagen having a faster degradation rate may be utilized.

Absorption rates may also be manipulated by the nature of cross-linking or chemical bonding between the amniotic membrane extract and the collagen-based carrier. That is, if slow absorption is desired, then the amniotic membrane and collagen are bound with either, more bonds, tighter bonds and/or stronger bonds. If more rapid absorption is required, then the amniotic membrane and collagen or more loosely bound—for example using fewer and/or weaker and/or less tight chemical bonds.

In one embodiment of the invention, absorption rates are controlled by a combination of collagen degradation rates and chemical bonding between amniotic membrane and collagen.

Collagen in human amniotic membrane is similar to the most widespread and important proteins found in the body. Collagen is an essential element for healing wounds anywhere in the body, including the eye. Therefore, in some embodiments of the invention, the inventive patch may be used to therapeutically treat damaged or diseased cornea, limbus and surrounding conjunctiva, in addition to other wounds and conditions.

Ideally, for clinical use, AM should be sterile and free of contamination. It should also be easy to obtain, transport, and store for long periods without deterioration. The most common preservation method, cryopreservation, requires an expensive and bulky −80° deep freezer to maintain the viability of AM for a long time; for instance, at −4° the AM has a storage time of about one month. These are limitations to the wider use of AM, particularly in developing countries. Freeze-dried AM offers important advantages over cryopreserved AM because it is free of contamination, may be easily transported and stored, and can be used readily with minimal preparation at the time of surgery. However, Radiation-sterilization at 25 and 35 kGy of freeze-dried human amniotic membranes caused degradative effects in the structural and biological and properties specifically the collagen protein and growth factors.

In one embodiment, the amniotic/collagen patch is manufactured as follows:

AM/Placental extract alone or mixed with collagen will be primed with aqueous medium (separate or together), surfactant and other solids to form a homogenous suspension with different concentrations. Such components can be obtained commercially from any suitable source or prepared. For example AM/placental extract (lyophilized or dried) can be obtained from human and/or mammalian source. In the manufacture of the patch:

The ratio of AM/placental extract to collagen range from 0.1-100:100-0.1.

Any suitable buffer or liquid can be used to prepare the formulation. Range 0.01%-50% by weight.

The homogenate can be mixed at any suitable speed, temperature, or other parameters that maintain its properties.

Surfactant such as Hydroxyethyl cellulose or polyethylene polypropylene glycol (0.001 to 1%) will be added to provide even distribution of the film, desired thickness & assist the dried device from the mold.

Other biologically accepted solids may be included to provide total solid concentration sufficient to cast a film upon the mold with desired consistency. Preferred range of about 0.5-3.0 wt %

The PH can be adjusted by using sodium or potassium hydroxide and phosphates, hydrochloric acid or any other biologically accepted buffer to keep physiological PH.

The above homogenate will be casted into semispherical shaped thermoplastic molds e.g. polycarbonate or polypropylene.

Drying method with adjusted temperature and humidity; one or two steps

Crosslinking using UV light to obtain the desired predetermined solubility.

Sterilization with gamma irradiation. (Can be used also for further crosslinking). Or with CO2 gas if proven safer than F-irradiation.

The product is packaged in suitable packaging.

It is important to use a suitable sterilization technique to eliminate microorganisms—yet without inducing changes in the protein chemistry, the mechanical properties and/or the degradation behavior of the AmnioShield. To that end, in one embodiment of the invention, Γ-irradiation is utilized for sterilization—as it is a reliable sterilization method and which does not significantly alter the chemical/mechanical properties. Preferably, a dose of 2.5 Mrad (25 KGY) is validated to achieve complete sterilization. Studies on the effect of γ-irradiation on collagen structure indicate minor fragmentation, which is compensated by the formation of additional cross-links that maintains the mechanical strength of collagen. At the same time the materials become more sensitive to enzymatic attack by collagenase and proteinase.

Potential Uses of the Inventive Patch

The main potential use of the AmnioShield is to maintain the ocular surface health and to promote healing after injury due to inflammation, infection, trauma or surgery. Because the patch contains naturally active ingredients, it would appear to be an ideal alternative to bandage contact lenses for protecting the eye. As noted earlier, the patch may be an essential part of the natural wound healing process. It can also serve as a prototype of a delivery system for biochemical or biological components for the eye.

In another embodiment of the invention, the AmnioShield also is a drug delivery system. In this embodiment, the AmnioShield is impregnated or otherwise provided with drugs such as antibiotics, vitamins or other medicines that are to be applied to a bodily site. The drugs, as such, are delivered directly to a site where they are needed. As mentioned above, the timing of drug delivery may be manipulated by choosing a collagen or another carrier with a desired degradation rate.

Still in other embodiments of the invention, the novel amniotic/placental extract preparation with or without collagen proteins is prepared in a gel or cream form for internal/external application. The gel or cream may be applied as a tissue filler or as a healing aid as described herein.

Examples of possible uses of the AnmioShied for various treatments include:

1) Treatment of Dry Eye Syndrome:

As proposed, over time, the patch will dissolve, become gel-like, and eventually liquefy. This gel-like dissolution can be very helpful to individuals who do not produce sufficient quantities of tears. This "dry eye" condition can re-damage the healed ocular surface. Therefore, the patch not only promotes healing, but it also protect the newly formed ocular surface epithelium by keeping the eye lubricated to avoid blinking microtrauma.

2) Treatment of Corneal Trauma Caused by Chemical or Thermal Injury:

The inventive patch has the potential to reduce scarring if applied as a bandage contact lens within 24-48 hours after acute injury. This lens could reduce the inflammation and neovascularization, and thus the risk of blindness and post-treatment corneal graft, when compared with existing treatments.

3) Treatment of Non-Healing Corneal Ulceration:

Superficial corneal ulcers secondary to trauma, infection, disease of after surgery.

4) Post-Refractive Treatment:

Postoperative complications after refractive surgery include pain, epithelial defect, and/or haze. The inventive patch may present an effective solution to solve these critical problems after photorefractive keratectomy (PRK).

In other embodiments of the invention different embodiments of the AmnioShield are utilize in a wide variety of clinical applications. It will be understood by one of ordinary skill in the art that the AmnioShield device may need to be adapted for various uses, but they are all based on the same inventive concept of embedding or binding amniotic/placental extract with collagen proteins or other biological materials.

The following are non-limiting examples of clinical uses of the AmnioShield according to different embodiments of the invention:

Wound Repair:
- In some embodiments, a composition containing amniotic membrane/placenta-collagen complex disclosed herein is used as a wound covering or is used to facilitate wound repair.
- In some embodiments, the membrane/placenta-collagen complex is used to treat tissue is damaged, compromised, or lost due to an injury (e.g., a burn; a surgical incision; an area of necrosis resulting from an infection, trauma, or a toxin; a laceration).
- In some embodiments, the composition is applied to a wound in the skin (e.g., an incision, laceration, abrasion, ulcer, puncture, penetration)
- In some embodiments, the ulcer is a foot ulcer (e.g., a diabetic foot ulcer or an arterial insufficiency ulcer).
- In certain embodiments, is the use of the complex disclosed herein in different shape for repairing, reconstructing, replacing, or as a filler to replace missing soft tissue Nerve Injury:
- In some embodiments, the complex disclosed herein is used for repairing, reconstructing, replacing, or supplementing a recipient's damaged, compromised, or missing nerve tissue.
- In some embodiments, the complex disclosed herein is used as a covering over a nerve, a nerve graft, nerve transfer, or a repaired nerve (e.g., a peripheral nerve injury).
- In some embodiments, the complex disclosed herein is used to prevent or minimize scar formation, encapsulation, chronic compression, tethering of a nerve, and nerve entrapment.

Scarring:
- In some embodiments, the complex disclosed herein is used to prevent or reduce scarring in a subject in need thereof before during or after surgery.
- In some embodiments, a method disclosed herein is used to prevent or reduce the formation of a scar on an eye or on the surrounding tissue
- In some embodiments, the complex disclosed herein is used as a spacer between different layers of soft tissue.

Having described this invention with regard to specific embodiments, it is to be understood that the description is not meant as a limitation since further modifications and variations may be apparent or may suggest themselves to those skilled in the art. It is intended that the present application cover all such modifications and variations.

What is claimed is:

1. A method of producing a dissolvable patch formed into the shape of a contact lens comprising any one of an amniotic membrane extract and/or placental extract, said method comprising the steps of:
   providing any one of amniotic membrane extract, or placenta extract;
   providing a degradable carrier material;
   priming said degradable carrier and any one of said amniotic membrane extract or placenta extract with surfactant, and with other solids to form a homogenous suspension;
   mixing said homogenous suspension;
   casting said homogenous suspension in a semispherical mold to form said patch into the shape of a contact lens;
   whereby said patch formed in the shape of a contact lens dissolves over time in a patient's eye.

2. The method of claim 1, further comprising the step of chemical bonding any one of said amniotic membrane extract, or said placenta extract to said degradable carrier.

3. The method of claim 2, further comprising the step of selecting a bond strength to control absorption of one of said amniotic membrane extract, or placenta extract.

4. The method of claim 1, further comprising the step of selecting a degradation rate of said carrier to control absorption of one of said amniotic membrane extract, or placenta extract.

* * * * *